US009417110B2

(12) United States Patent
Raz et al.

(10) Patent No.: US 9,417,110 B2
(45) Date of Patent: Aug. 16, 2016

(54) ACCELERATED BENCH-TESTING OF MEDICAL DEVICES

(75) Inventors: Sagi Raz, Tel Aviv (IL); Raphael Benary, Tel Aviv (IL); Alon Shalev, Ra'anana (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 797 days.

(21) Appl. No.: 13/878,728

(22) PCT Filed: Oct. 10, 2011

(86) PCT No.: PCT/IL2011/000801
§ 371 (c)(1),
(2), (4) Date: Jun. 17, 2013

(87) PCT Pub. No.: WO2012/049679
PCT Pub. Date: Apr. 19, 2012

(65) Prior Publication Data
US 2013/0261994 A1    Oct. 3, 2013

Related U.S. Application Data

(60) Provisional application No. 61/392,059, filed on Oct. 12, 2010.

(51) Int. Cl.
*G01N 3/32* (2006.01)
*G01M 99/00* (2011.01)
(Continued)

(52) U.S. Cl.
CPC ............. *G01F 17/00* (2013.01); *G01M 99/007* (2013.01); *G01N 3/32* (2013.01)

(58) Field of Classification Search
CPC ............... A61F 2/2472; G01M 99/00; G01N 2203/0073; G01N 2203/0476; G01N 3/32; G01N 2203/0246; G01N 2203/0274; G01N 3/12; G01N 3/36; Y10S 623/912
See application file for complete search history.

(56) References Cited

U.S. PATENT DOCUMENTS 4,381,663 A * 5/1983 Swanson .................. G01N 3/36
73/168
4,546,642 A * 10/1985 Swanson ............... A61F 2/2472
73/168

(Continued)

FOREIGN PATENT DOCUMENTS

WO    2009/003081 A2    12/2008
WO    2009/157966 A1    12/2009

(Continued)

OTHER PUBLICATIONS

U.S. Appl. No. 61/392,059, filed Oct. 12, 2010.

(Continued)

*Primary Examiner* — David A Rogers
(74) *Attorney, Agent, or Firm* — Sughrue Mion, PLLC

(57) ABSTRACT

A biomedical tester includes a fluid-control container, shaped to define a fluid-control container port and a first interface surface defining fluid-control container apertures. A fluid controller is shaped to define a second interface surface defining controller ports. These elements and a motor are arranged to relative translation between the first and second interface surfaces; thereby effecting a time-varying overlap between subgroups of the system. Fixtures allow disposition therewithin of respective medical devices. Each of the fixtures includes one or more fixture first ports and fixture second ports. The fixture first ports are mounted in fluid Communication respective with the controller ports. A fluid pump includes first and second pump ports in fluid communication with the fixture second ports and the fluid-control container port, respectively.

31 Claims, 13 Drawing Sheets

(51) Int. Cl.
*A61F 2/24* (2006.01)
*G01F 17/00* (2006.01)

(56) References Cited

U.S. PATENT DOCUMENTS

| | | | | |
|---|---|---|---|---|
| 4,682,491 | A * | 7/1987 | Pickard | A61F 2/2472 |
| | | | | 73/168 |
| 4,972,721 | A * | 11/1990 | Conti | G01N 3/12 |
| | | | | 73/37.5 |
| 5,327,774 | A * | 7/1994 | Nguyen | A61F 2/2472 |
| | | | | 73/37 |
| 5,670,708 | A * | 9/1997 | Vilendrer | G01N 3/12 |
| | | | | 73/37 |
| 5,792,603 | A * | 8/1998 | Dunkelman | C12M 41/00 |
| | | | | 435/1.2 |
| 6,881,224 | B2 | 4/2005 | Kruse et al. | |
| 7,254,988 | B2 | 8/2007 | Keeble | |
| 7,326,564 | B2 * | 2/2008 | Lundell | A61F 2/2472 |
| | | | | 435/284.1 |
| 7,363,821 | B2 * | 4/2008 | Black | G01N 3/32 |
| | | | | 73/810 |
| 7,472,604 | B2 | 1/2009 | Moore, Jr. et al. | |
| 7,546,775 | B2 | 6/2009 | Chinavare | |
| 7,587,949 | B2 | 9/2009 | Dingmann et al. | |
| 7,621,192 | B2 * | 11/2009 | Conti | G01N 3/56 |
| | | | | 623/912 |
| 7,624,648 | B2 | 12/2009 | Nickel et al. | |
| 8,196,478 | B2 * | 6/2012 | Lorenz | A61F 2/82 |
| | | | | 73/818 |
| 8,490,504 | B2 * | 7/2013 | Weinberg | G01N 3/36 |
| | | | | 73/760 |
| 8,567,268 | B2 * | 10/2013 | Sun | G05D 22/02 |
| | | | | 73/431 |
| 8,627,708 | B2 * | 1/2014 | McCloskey et al. | G01N 3/32 |
| | | | | 73/37 |
| 9,237,935 | B2 * | 1/2016 | McCloskey et al. | G01N 3/32 |
| 2002/0116054 | A1 * | 8/2002 | Lundell | A61F 2/2472 |
| | | | | 623/2.1 |
| 2002/0173724 | A1 | 11/2002 | Dorando et al. | |
| 2003/0110830 | A1 * | 6/2003 | Dehdashtian | A61F 2/07 |
| | | | | 73/37 |
| 2003/0199083 | A1 * | 10/2003 | Vilendrer | C12M 21/08 |
| | | | | 435/297.2 |
| 2004/0016301 | A1 | 1/2004 | Moreno et al. | |
| 2006/0276882 | A1 | 12/2006 | Case et al. | |
| 2007/0168066 | A1 | 7/2007 | Grishaber et al. | |
| 2008/0243284 | A1 | 10/2008 | Grishaber et al. | |
| 2009/0180657 | A1 | 7/2009 | Isvan | |
| 2010/0225478 | A1 | 9/2010 | McCloskey et al. | |
| 2010/0242620 | A1 | 9/2010 | Lorenz et al. | |
| 2010/0291524 | A1 * | 11/2010 | Iwasaki | G01N 3/32 |
| | | | | 434/272 |
| 2011/0146385 | A1 * | 6/2011 | Weinberg | G01N 3/36 |
| | | | | 73/37 |

FOREIGN PATENT DOCUMENTS

| | | |
|---|---|---|
| WO | 2010/008674 A2 | 1/2010 |
| WO | 2012/049679 A2 | 4/2012 |

OTHER PUBLICATIONS

An International Search Report and a Written Opinion both dated May 8, 2012, which issued during the prosecution of Applicant's PCT/IL2011/000801.

An International Preliminary Report on Patentability dated Apr. 16, 2013, which issued during the prosecution of Applicant's PCT/IL2011/000801.

ElectroForce® Stent/Graft Test Instruments for Pulsatile Distention (2009; month unknown), The ElectroForce® Systems Group of Bose® Corporation (Eden Prairie, Minnesota).

ElectroForce® Test Instruments (2010; month unknown), The ElectroForce® Systems Group of Bose® Corporation (Eden Prairie, Minnesota).

ElectroForce® Multi-specimen High Cycle Fatigue Test Instruments (2009; month unknown), The ElectroForce® Systems Group of Bose® Corporation (Eden Prairie, Minnesota).

ElectroForce® 3200 DMA Test Instrument (2010; month unknown), The ElectroForce® Systems Group of Bose® Corporation (Eden Prairie, Minnesota).

ElectroForce® 9210 Drug-Eluting Stent Test Instrument (2010; month unknown), The ElectroForce® Systems Group of Bose® Corporation (Eden Prairie, Minnesota).

"ElectroForce® Stent/Graft Test Instruments" webpage (http://www.bose-electroforce.com/product.cfm?pid=5), downloaded Sep. 20, 2010, The ElectroForce® Systems Group of Bose® Corporation (Eden Prairie, Minnesota) (earliest date of publication not known).

\* cited by examiner

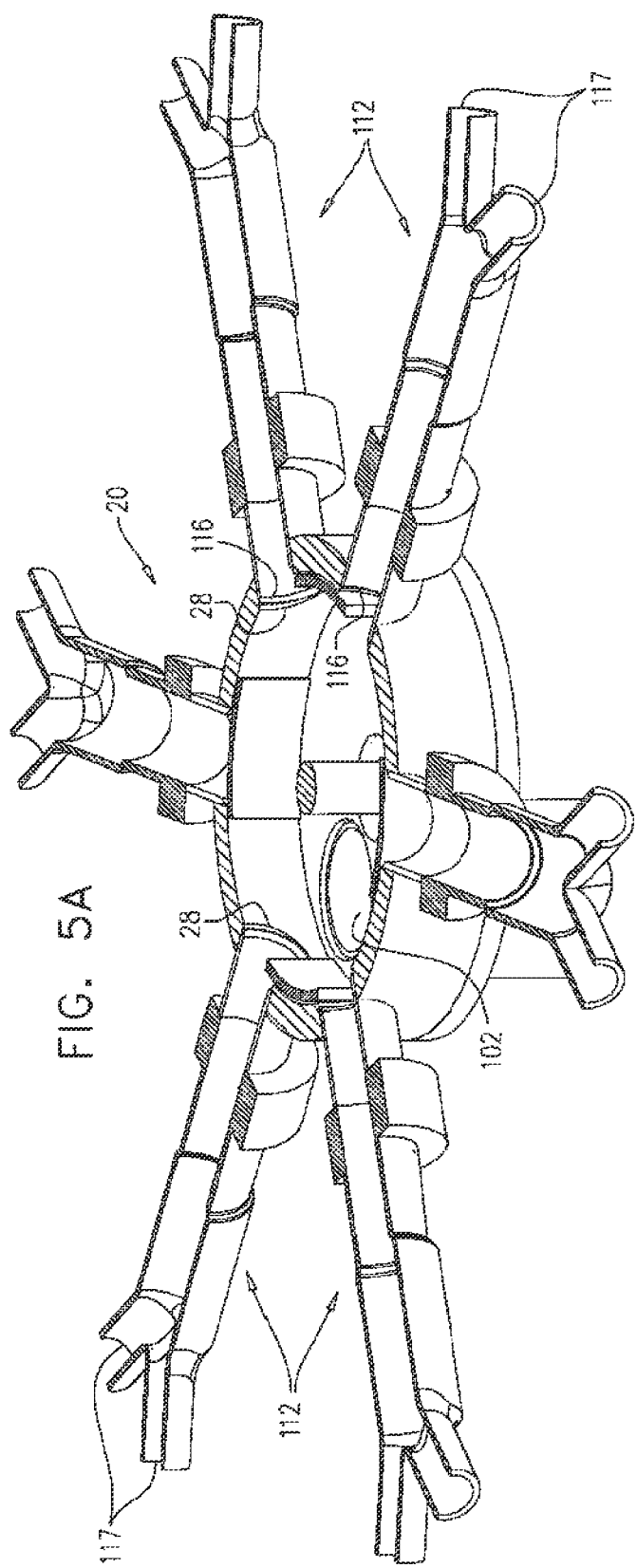

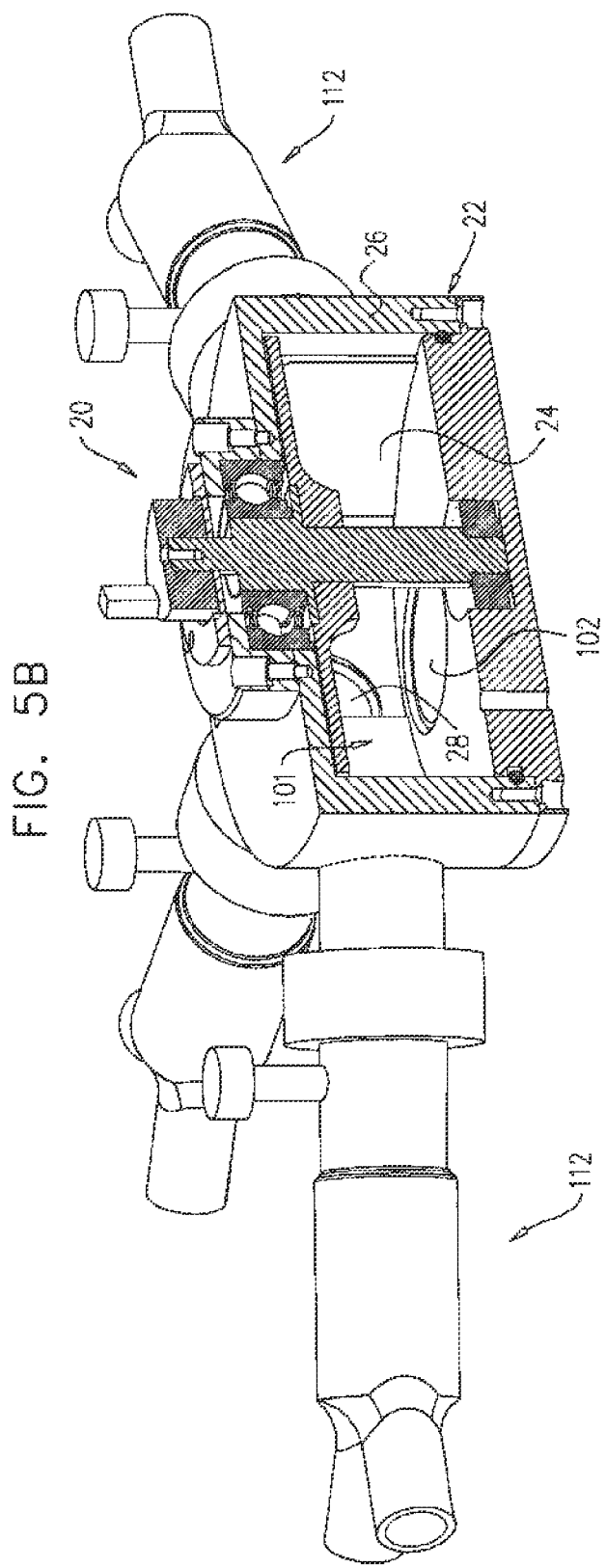

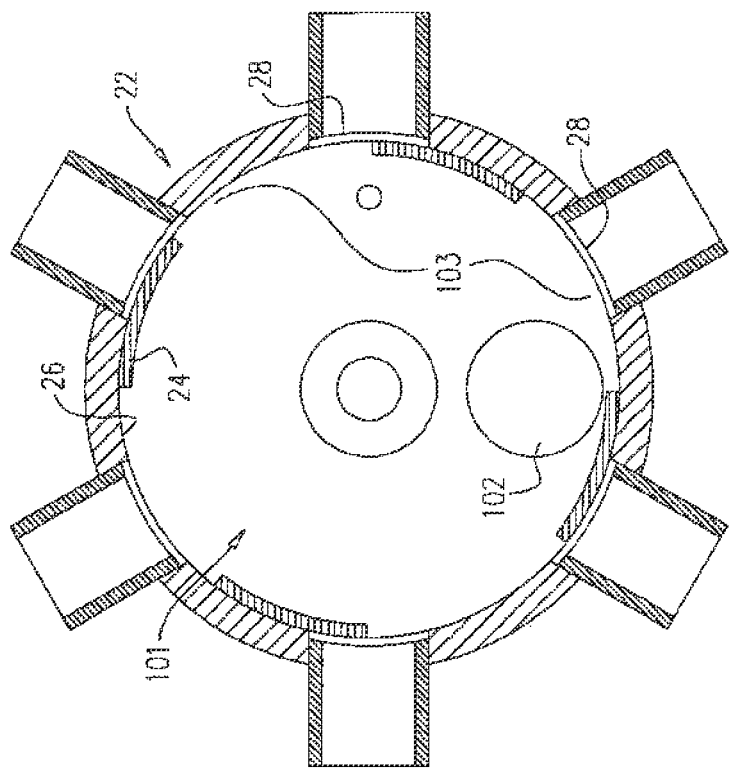
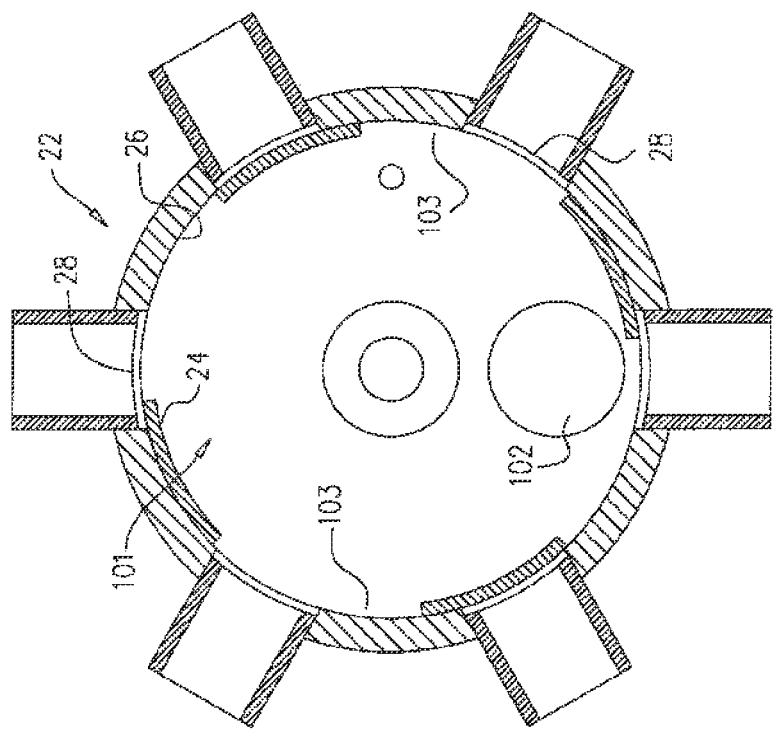

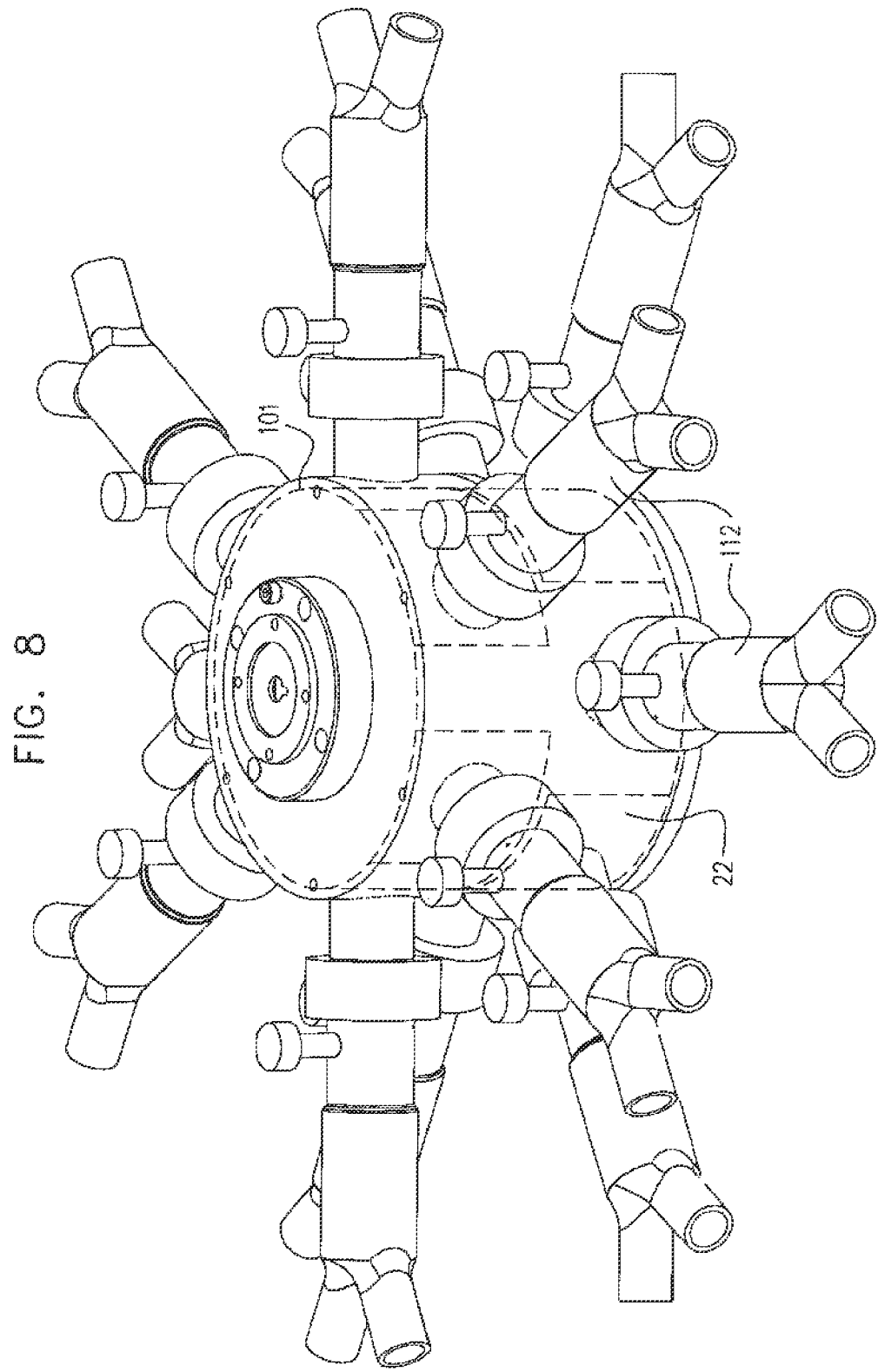

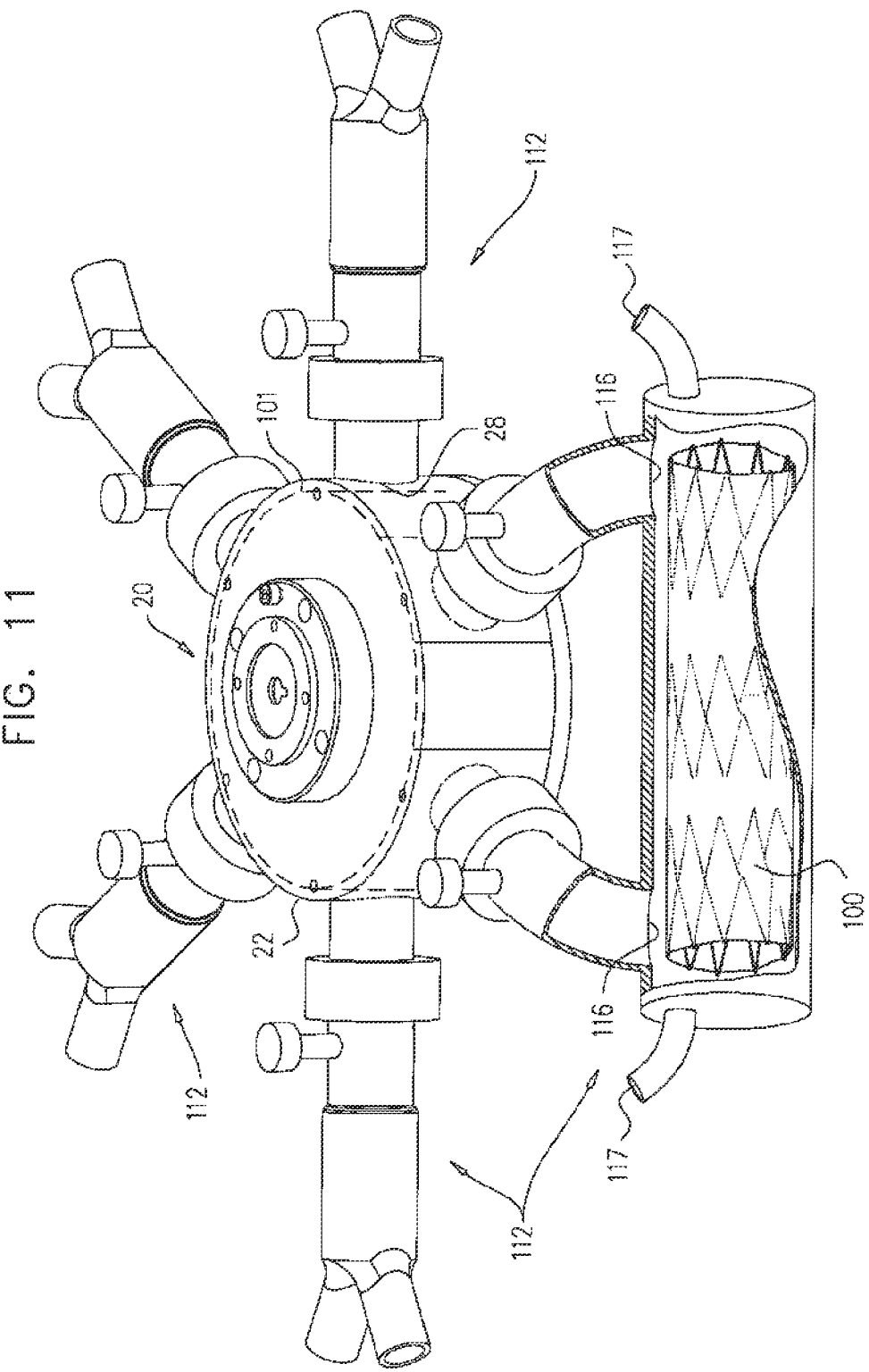

ACCELERATED BENCH-TESTING OF MEDICAL DEVICES

CROSS-REFERENCE TO RELATED APPLICATIONS

The present application is the US national stage of International Application PCT/IL2011/000801, filed Oct. 10, 2011, which claims priority from U.S. Provisional Application 61/392,059, filed Oct. 12, 2010, which is assigned to the assignee of the present application and is incorporated herein by reference.

FIELD OF THE APPLICATION

The present invention relates generally to apparatus and methods for fatigue testing, and specifically to apparatus and methods for accelerated fatigue testing of implantable medical devices.

BACKGROUND OF THE INVENTION

Vascular prostheses, such as stents, grafts, and stent-grafts, are used for repairing vascular abnormalities, such as abdominal aortic aneurysm (AAA). Because implanted vascular prostheses are subjected to continuous changes in blood pressure and other physiological stresses, they must be fatigue-tested during product development and regulatory approval processes. Commercially-available fatigue test instruments generally offer accelerated testing using standing pressure waves acting on both sides of the medical device being tested. The resulting wave causes an increase in pressure which results in radial expansion. Typically, the maximum frequency achievable in actual use of such test instruments is 20 Hz. Fatigue test instruments generally test primarily radial expansion of the medical device, rather than axial loading.

SUMMARY OF THE APPLICATION

In some embodiments of the present invention, a biomedical tester is provided for fatigue testing one or more medical devices. The biomedical tester periodically increases and decreases the pressure of a fluid in contact with the medical devices, in order to simulate the pulsatile pressure within human blood vessels. The tester generates in vitro conditions that simulate in vivo radial and axial load of the medical devices, by periodically injecting a measured amount of fluid into the medical devices during each of a large number of cycles. The tester is typically configured such that the fluid flows in a single direction through each of the medical devices, rather than periodically reversing direction at high frequency. The tester tests axial loading because the motion of the fluid within each of the medical devices pushes, by way of shear, the medical device axially forward within a fixture of the tester, and thereafter, if the medical device is anchored to the fixture, the medical device springs backward.

For some applications, in order to effect the periodic increases and decreases in pressure, the tester comprises a first interface surface that is shaped so as to define one or more apertures, and a second interface surface that is shaped so as to define one or more ports. A motor of the tester effects relative translation between the first and second interface surfaces, thereby effecting a time-varying overlap between at least a subgroup of the apertures and at least a subgroup of the ports. Whenever one of the apertures overlaps a given port, fluid flows through the aperture into the port. Whenever none of the apertures overlaps a given port, the first interface surface blocks fluid flow into the port.

For some applications, the tester comprises a fluid control assembly; one or more fixtures, configured to allow disposition therewithin of respective ones of the medical devices; and a fluid pump. The fluid control assembly comprises a fluid-control container, a fluid controller, and a motor. The fluid-control container is shaped so as to define the first interface surface, which, as mentioned above, is shaped so as to define the apertures. The fluid controller is shaped so as to define the second interface surface, which, as mentioned above, is shaped so as to define the ports. The fluid-control container, fluid controller, and motor are arranged to effect relative translation between the first and second interface surfaces, thereby effecting a time-varying overlap between at least a subgroup of the apertures and at least a subgroup of the ports. The fixtures comprise respective fixture first and second ports. The fixture first ports are mounted in fluid communication with respective ones of the ports of the second surface. The fluid pump comprises first and second pump ports, which are in fluid communication with the fixture second ports and a port of the fluid-control container, respectively. The tester is typically configured to pump fluid therethrough in a closed loop.

For some applications, the medical devices comprise stents, grafts, or stent-grafts used for repairing vascular abnormalities, such as an abdominal aortic aneurysm (AAA). Some such stent-grafts for treating AAA have a plurality of modules that are coupled to one another, such as during an implantation procedure. In stent-grafts for treating AAA, radial expansion typically occurs primarily at the proximal neck of the aneurism and at the distal end of the iliac artery. The tester may be configured to focus testing on (a) the anastomosis regions between modules of the stent-graft, such as by placing an end of a first stent-graft overlapping with an end of a second stent-graft, and/or (b) the attachment of a stent-graft to the wall of a blood vessel, such as by attaching the stent-graft to the wall of a fixture of the tester (for example, using barbs of the stent-graft). These regions experience axial forces that fatigue struts of the stent-graft, and radial pressure that fatigues graft material of the stent-graft (since the radial expansion of the graft is negligible and the struts barely move). The tester may thus be used for evaluating the long-term dimensional and structural integrity of the implant anastomosic region(s).

There is therefore provided, in accordance with an application of the present invention, apparatus for fatigue testing one or more medical devices, the apparatus including:
  a fluid control assembly, which includes:
    a fluid-control container, which is shaped so as to define a fluid-control container port and a first interface surface that is shaped so as to define one or more fluid-control container apertures;
    a fluid controller, which is shaped so as to define a second interface surface that is shaped so as to define one or more controller ports; and
    a motor,
    wherein the fluid-control container, the fluid controller, and the motor are arranged to effect relative translation between the first and second interface surfaces, thereby effecting a time-varying overlap between at least a subgroup of the fluid-control container apertures and at least a subgroup of the controller ports;
  one or more fixtures, configured to allow disposition therewithin of respective ones of the medical devices, each of which fixtures includes one or more fixture first ports and one or more fixture second ports, which fixture first ports are mounted in fluid communication with respective ones of the controller ports; and a fluid pump, which includes first and second pump ports, which are in fluid communication with the fixture second ports and the fluid-control container port, respectively.

For some applications, throughout steady-state operation of the apparatus, the fluid pump is configured to exclusively pump fluid out of exactly one of the first and second pump ports throughout at least one period having a duration of at least one second, such as at least one hour.

For some applications, throughout steady-state operation of the apparatus, the fluid pump is configured to exclusively pump fluid out of exactly one of the first and second pump ports throughout a test of the medical devices.

For some applications, the apparatus is configured to cyclically increase and decrease a pressure of a fluid within the fixtures during a plurality of cycles.

For some applications, throughout steady-state operation of the apparatus, the fluid pump is configured to exclusively pump fluid out of exactly one of the first and second pump ports throughout at least one of the cycles, such as at least two of the cycles.

For some applications, the fluid pump is configured to receive fluid via the first pump port, which thus serves as an inlet, and to pump the fluid out of the second pump port, which thus serves as an outlet, such that the fluid flows through the apparatus along a flow path:

out of the outlet, into the fluid-control container port, which thus serves as a container input port, through the fluid-control container apertures, such that the fluid-control container serves as a fluid-distribution container, through the controller ports, such that the fluid controller serves as a fluid distributor, into the fixture first ports, which thus serve as fixture input ports, out of the fixture second ports, which thus serve as fixture output ports, and into the inlet of the fluid pump.

Typically, the apparatus is configured to provide a closed loop for fluid flow therethrough.

For some applications; the overlap periodically varies at a rate of 10 to 150 Hz.

For some applications, the apparatus further includes a fluid.

For some applications, the first and second interface surfaces are cylindrical.

Alternatively, for some applications, the first and second interface surfaces are planar. For some applications, the fluid-control container, the fluid controller, and the motor are arranged such that the motor effects rotation of the fluid-control container with respect to the fluid controller, and the first and second interface surfaces define respective planes that are perpendicular to an axis of the fluid control assembly around which the motor effects the rotation.

For some applications, the apparatus further includes a fixture container, which is shaped so as to define a fixture container port that is in fluid communication with the first pump port, and the fixtures are disposed within the fixture container, such that the fixture second ports are in fluid communication with an interior of the fixture container, and with the first pump port via the interior of the fixture container and the fixture container port. For some applications, the apparatus further includes a fluid having a sufficient volume such that a level of the fluid within the fixture container is above a level of the fixture second ports. For some applications, the apparatus is configured such that the fixture container remains stationary during operation of the apparatus. For some applications, the fixture container is shaped so as to define a plurality of walls, and the apparatus is configured such that the second surface serves as at least one of the walls of the fixture container. For some applications, the apparatus further includes a fluid guide, which connects the fixture container port and the first pump port in fluid communication. For some applications, the apparatus further includes a pressure sensor, which is in fluid communication with the fixture container. For some applications, the apparatus further includes a pressure relief valve, which is in fluid communication with the fixture container.

For some applications, the apparatus further includes a heating element, which is in fluid communication with the fixture container.

For some applications, the fluid-control container, the fluid controller, and the motor are arranged such that the motor effects rotation of the fluid-control container with respect to the fluid controller. For some applications, the fluid-control container, the fluid controller, and the motor are arranged such that the motor effects the rotation of the fluid-control container. Alternatively or additionally, the fluid-control container, the fluid controller, and the motor are arranged such that the motor effects the rotation of the fluid controller. For some applications, the fluid-control container and the fluid controller are disposed around a common axis. For some applications, the apparatus further includes a rotation counter, which is configured to count a number of relative rotations of the fluid-control container with respect to the fluid controller.

For some applications, the motor is in mechanical communication with the fluid-control container. For some applications, the fluid-control container and the motor are arranged such that the motor effects rotation of the fluid-control container. For some applications, the fluid control assembly further includes a motor shaft, a first end of which is coupled to the motor, and a second end of which is coupled to the fluid-control container.

For some applications, the motor is in mechanical communication with the fluid controller. For some applications, the fluid controller and the motor are arranged such that the motor effects rotation of the fluid controller. For some applications, the fluid control assembly further includes a motor shaft, a first end of which is coupled to the motor, and a second end of which is coupled to the fluid controller.

For some applications, at least a portion of the medical devices are medical device components, and at least a portion of the fixtures are configured to allow disposition therewith of respective ones of the medical device components.

For some applications, the apparatus further comprises one or more flow straighteners, which are positioned near respective ones of the fixture first ports, and which are configured to cause fluid to flow through the respective fixtures generally parallel to respective longitudinal axes of the fixtures For some applications, the apparatus further includes a fluid guide, which connects the second pump port and the fluid-control container port in fluid communication. For some applications, the apparatus further includes an O-ring, which is disposed between the fluid guide and the fluid-control container port.

For some applications, the fluid-control container apertures are generally equally spaced along the first interface surface.

For some applications, the distributor ports are generally equally spaced along the second interface surface.

For some applications, at least one of the fluid-control container apertures is shaped so as to define a rectangle. For some applications, at least one of the controller ports is shaped so as to define an ellipse.

For some applications, at least one of the fluid-control container apertures is shaped so as to define an ellipse.

For some applications, at least one of the controller ports is shaped so as to define a shape selected from the group consisting of: a rectangle and an ellipse.

For some applications, the apparatus further includes a pressure sensor, which is in fluid communication with the fluid-control container.

For some applications, the apparatus further includes a signal-conditioning circuit. For some applications, the apparatus further includes a graphical user interface, and the signal-conditioning circuit is configured to convert an output of the pressure sensor for display on the graphical user interface. For some applications, the apparatus further includes a processing unit, which is coupled to the signal-conditioning circuit, and which is configured to control a speed of the motor so as to maintain a value of a fluid pressure within a user-defined range, which value is measured by the pressure sensor. For example, the user-defined range of the fluid pressure may have a lower limit of between 50 and 70 mmHg and a higher limit of between 160 and 200 mmHg.

For some applications, the apparatus is configured to maintain a range of fluid pressure having a lower limit of between 50 and 70 mmHg and a higher limit of between 160 and 200 mmHg. For some applications, the overlap periodically varies at a rate of 10 to 150 Hz.

For some applications, the apparatus further includes a pressure relief valve, which is in fluid communication with the fluid-control container.

For some applications, the apparatus further includes a heating element, which is in fluid communication with the fluid-control container.

For some applications, the apparatus further includes a user interface, which is configured to enable setting of operational parameters of the heating element so as to maintain a temperature of fluid within the apparatus within a user-defined range. For example, the user-defined range may have a lower limit of between 35 and 37 degrees and a higher limit of between 37 and 39 degrees centigrade.

For some applications, the fixtures are generally tubular and have respective first and second ends. For some applications, the fixture first ports of at least one of the fixtures include two fixture first ports, which are disposed near the first and second ends of the first fixture, respectively. For some applications, the two fixture first ports are disposed less than respective distances from the first and second ends of the first fixture, each of which distances being equal to 5 times a square root of an average cross-sectional area of the fixture. For some applications, the two fixture first ports are mounted in fluid communication with respective ones of the controller ports. For some applications, the fixture second ports of at least one of the fixtures include two fixture second ports, which are disposed near the first and second ends of the first fixture, respectively. For some applications, the two fixture second ports are disposed less than respective distances from the first and second ends of the first fixture, each of which distances being equal to 10 times a square root of an average cross-sectional area of the fixture.

For any of the applications described above, the apparatus may further include at least 5 liters of saline solution.

For any of the applications described above, the apparatus may further include between 5 and 200 liters of fluid.

For any of the applications described above, at least one of the fixtures may have an individual volume of between 30 and 400 ml.

For any of the applications described above, the apparatus may further include the medical devices.

There is further provided, in accordance with an application of the present invention, a method including:

providing a biomedical tester, which includes (a) a fluid control assembly, which includes (i) a fluid-control container, which is shaped so as to define a fluid-control container port and a first interface surface that is shaped so as to define one or more fluid-control container apertures, (ii) a fluid controller, which is shaped so as to define a second interface surface that is shaped so as to define one or more controller ports, and (iii) a motor, wherein the fluid-control container, the fluid controller, and the motor are arranged to effect relative translation the first and second interface surfaces, thereby effecting a time-varying overlap between at least a subgroup of the fluid-control container apertures and at least a subgroup of the controller ports; (b) one or more fixtures, configured to allow disposition therewithin of respective ones of the medical devices, each of which fixtures includes one or more fixture first ports and one or more fixture second ports, which fixture first ports are mounted in fluid communication with respective ones of the controller ports; and (c) a fluid pump, which includes first and second pump ports, which are in fluid communication with the fixture second ports and the fluid-control container port, respectively;

disposing one or more medical devices in respective ones of the fixtures of the biomedical tester; and activating the biomedical tester to test the one or more medical devices.

For some applications, the biomedical tester is configured to cyclically increase and decrease a pressure of a fluid within the fixtures during a plurality of cycles, and activating includes activating the biomedical tester for at least 30 million of the cycles.

For some applications, activating the biomedical tester includes activating the biomedical tester such that, throughout steady-state operation of the biomedical tester, the fluid pump exclusively pumps fluid out of exactly one of the first and second pump ports throughout at least one period having a duration of at least one second, such as at least one hour.

For some applications, activating the biomedical tester includes activating the biomedical tester such that, throughout steady-state operation of the biomedical tester, the fluid pump exclusively pumps fluid out of exactly one of the first and second pump ports throughout a test of the medical devices.

For some applications, activating the biomedical tester includes activating the biomedical tester to cyclically increase and decrease a pressure of a fluid within the fixtures during a plurality of cycles For some applications, activating the biomedical tester includes activating the biomedical tester such that the overlap periodically varies at a rate of 10 to 150 Hz.

For some applications; providing the biomedical tester includes:

providing the biomedical tester further including a fixture container, which is shaped so as to define a fixture container port that is in fluid communication with the first pump port, wherein the fixtures are disposed within the fixture container, such that the fixture second ports are in fluid communication with an interior of the fixture container, and with the first pump port via the interior of the fixture container and the fixture container port; and placing a fluid in the fixture container that has a sufficient volume such that a level of the fluid within the fixture container is above a level of the fixture second ports.

For some applications, at least a portion of the medical devices are medical device components, and disposing the one or more medical devices includes disposing the medical device components in at least a portion of the fixtures.

For any of the applications described above, providing the biomedical tester may include placing at least 5 liters of saline solution in the biomedical tester.

For any of the applications described above, providing the biomedical tester may include placing between 5 and 200 liters of fluid in the biomedical tester.

For any of the applications described above, providing the biomedical tester may include providing the biomedical tester in which at least one of the fixtures has an individual volume of between 30 and 400 ml.

The present invention will be more fully understood from the following detailed description of embodiments thereof, taken together with the drawings, in which:

BRIEF DESCRIPTION OF THE DRAWINGS

FIGS. 5A and 5B are schematic cross-sectional views of the fluid control assembly and fixtures of FIG. 4 taken along lines VA-VA and VB-VB of FIG. 4, respectively, in accordance with an application of the present invention;

FIGS. 6A-B are cross-sectional views of the fluid-control container and the fluid controller of FIGS. 1-2 in differing alignments with each other, in accordance with an application of the present invention;

FIGS. 8 and 9A-B are schematic illustrations of an alternative configuration of the tester of FIGS. 1-2, in accordance with an application of the present invention;

FIG. 11 is a schematic illustration of an alternative configuration of a fixture of the tester, in accordance with an application of the present invention.

DETAILED DESCRIPTION OF APPLICATIONS

Figure 1:
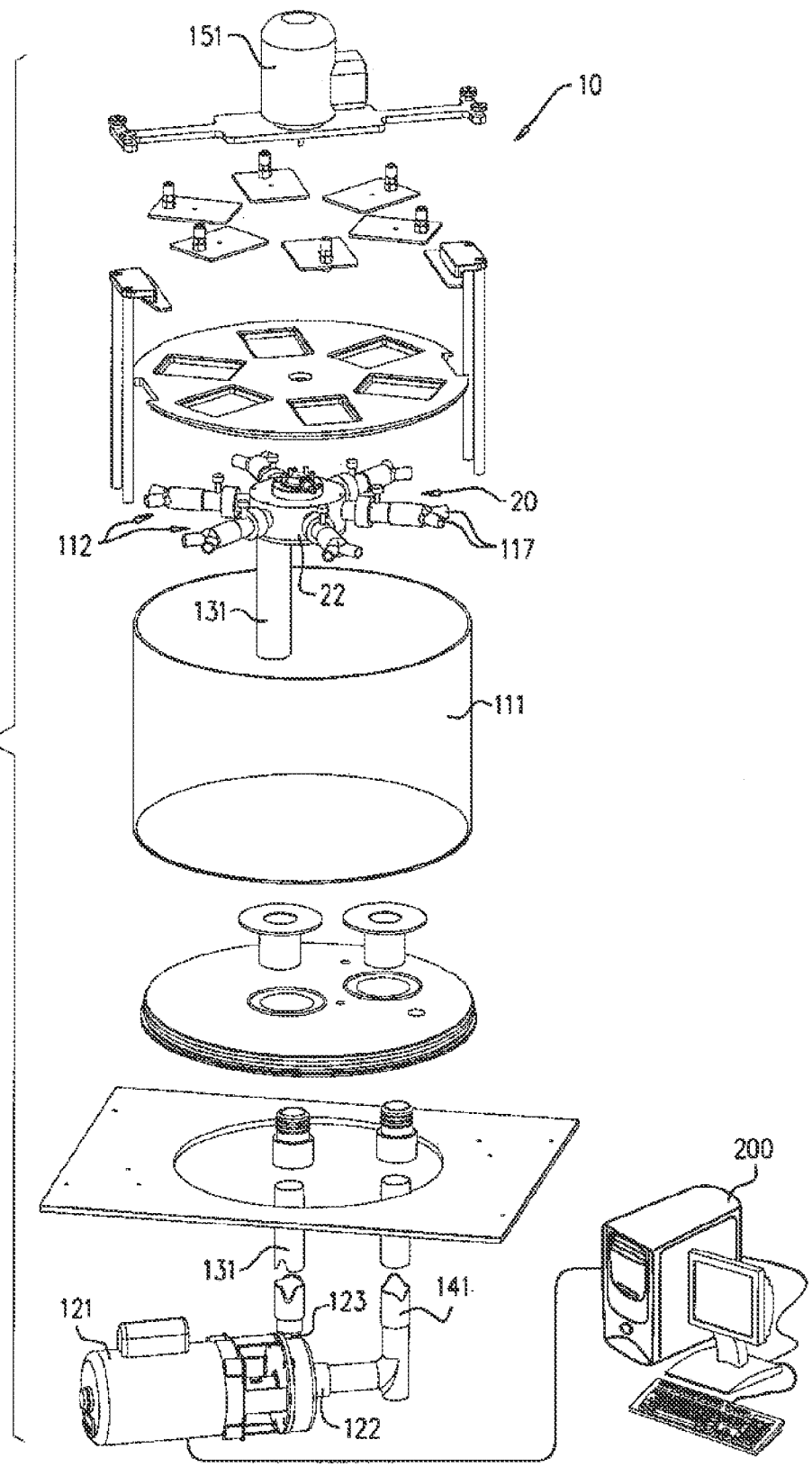
FIGS. 1 and 2 are schematic illustrations of a biomedical tester for fatigue testing one or more medical devices, in accordance with an application of the present invention.
Figure 2:
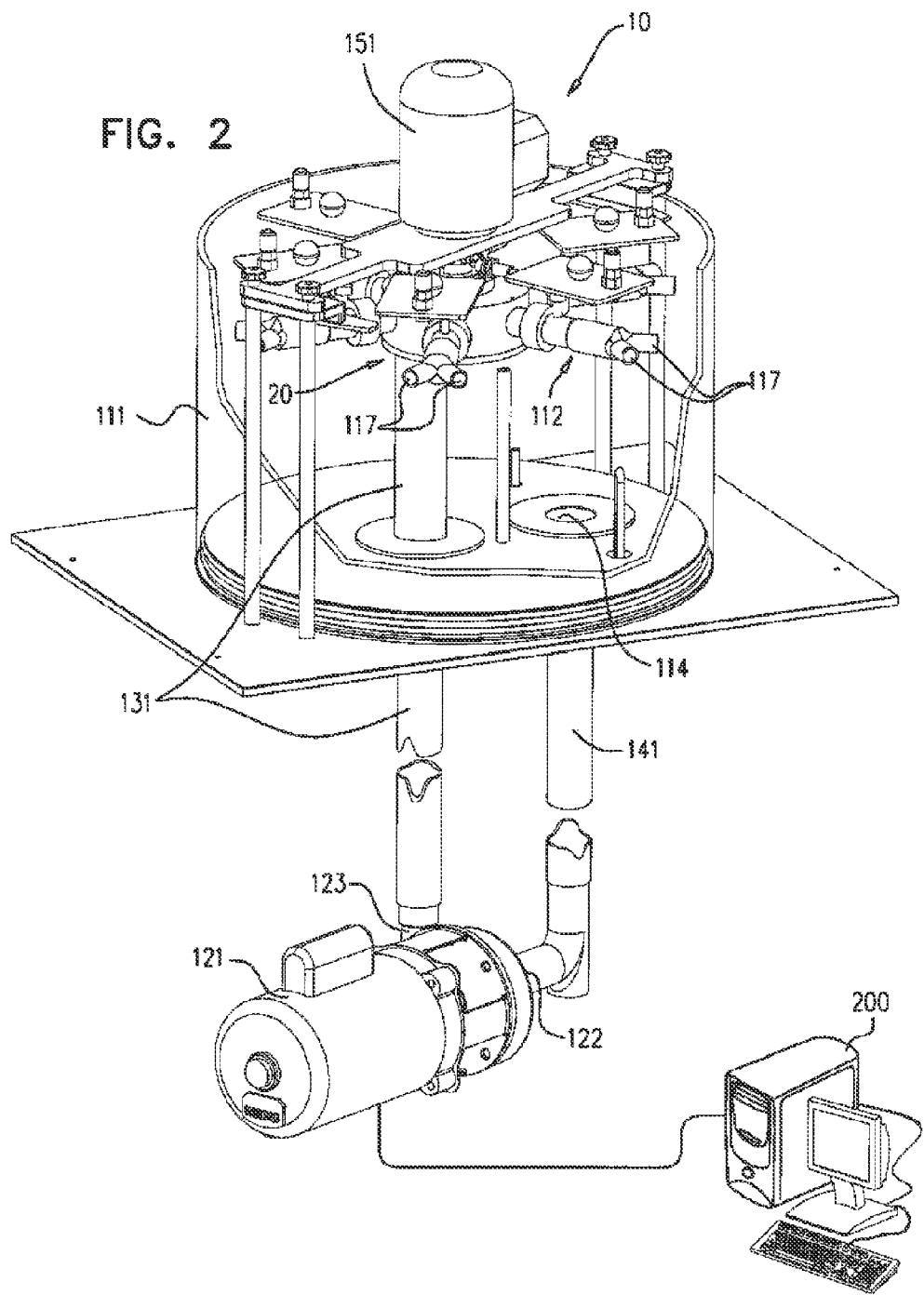

FIGS. 1 and 2 are schematic illustrations of a biomedical tester 10 for fatigue testing one or more medical devices, in accordance with an application of the present invention. FIG. 1 shows unassembled components of tester 10, while FIG. 2 shows the assembled tester. Tester 10 typically comprises a fluid control assembly 20, which helps control the flow of fluid through the tester, and one or more fixtures 112, which are configured to allow disposition therewithin of respective ones of the medical devices. Fluid control assembly comprises a motor 151. The motor need not operate in a pulsatile regimen, as is necessary in some commercially-available testers, and thus may be able to operate at a higher frequency than some commercially-available testers.

The tester cyclically increases and decreases the pressure of a fluid within fixtures 112 in contact with the medical devices, during a plurality of cycles, in order to simulate the pulsatile pressure within human blood vessels. For some applications, the tester is configured to repeatedly cycle between a higher pressure (e.g., 120-130 mmHg), which simulates systolic blood pressure, and a lower pressure (e.g., 75-85 mmHg), which simulates diastolic blood pressure. In general, a cycle of operation of tester 10 can be considered analogous to a mammalian heart rate cycle, albeit usually having a rate that is up to two orders of magnitude greater than a heart rate. For example, instead of a typical human heart rate of one beat per second (i.e., 1 Hz), tester 10 typically is configured to cycle at a rate of at least 80 Hz, at least 100 Hz, or even higher, so as to complete an overall simulated lifespan of a medical device in as short a time period as is reasonably possible. As used herein, including in the claims, a "cycle" includes one period of relatively lower pressure, and one period of relatively higher pressure; the lower-pressure period may follow or precede the higher-pressure period. For some applications, a rate of fluid flow through at least a portion of tester 10 (such as one or more of fixtures 112) cycles between a lower rate and a higher rate, typically synchronized with the cycling of the tester between the higher and lower pressures.

Typically, a total fluid-containing volume of tester 10 is at least 5 liters, no more than 200 liters (such as no more than 100 liters), and/or between 5 and 200 liters, between 5 and 100 liters, or between 5 and 80 liters, such as at least 10 liters, no more than 60 liters, and/or between 20 and 40 liters. Typically, the fluid comprises water or saline solution.

Figure 3:
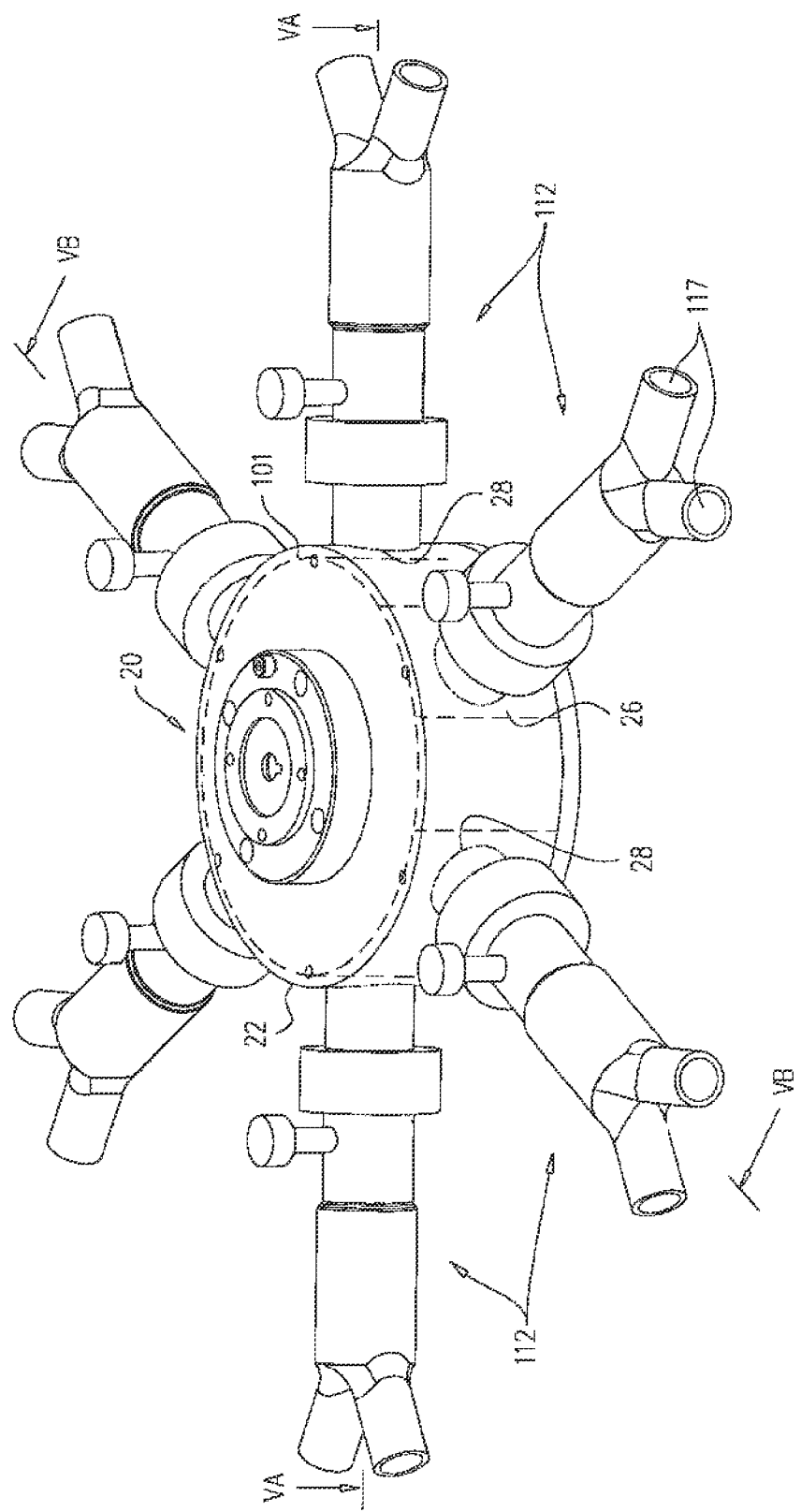
FIG. 3 is a schematic illustration of a portion of a fluid control assembly and fixtures of the tester of FIGS. 1-2, in accordance with an application of the present invention.

FIG. 3 is a schematic illustration of a portion of fluid control assembly 20 and fixtures 112; in accordance with an application of the present invention. In this configuration, fixtures 112 are arranged around the fluid control assembly, and extend outward from the fluid control assembly, like spokes from a hub. Tester 10 typically comprises at least 2 fixtures, not more than 20 fixtures, and/or between 2 and 10 fixtures 112, such as at least 3 fixtures, not more than 10 fixtures, and/or between 6 and 10 fixtures, e.g., 6 fixtures.

Fluid control assembly 20 comprises a fluid-control container 101 and a fluid controller 22. For some applications, such as shown in FIG. 3, fluid-control container 101 is disposed within fluid controller 22, such that the fluid controller surrounds the fluid-control container.

Figure 4:
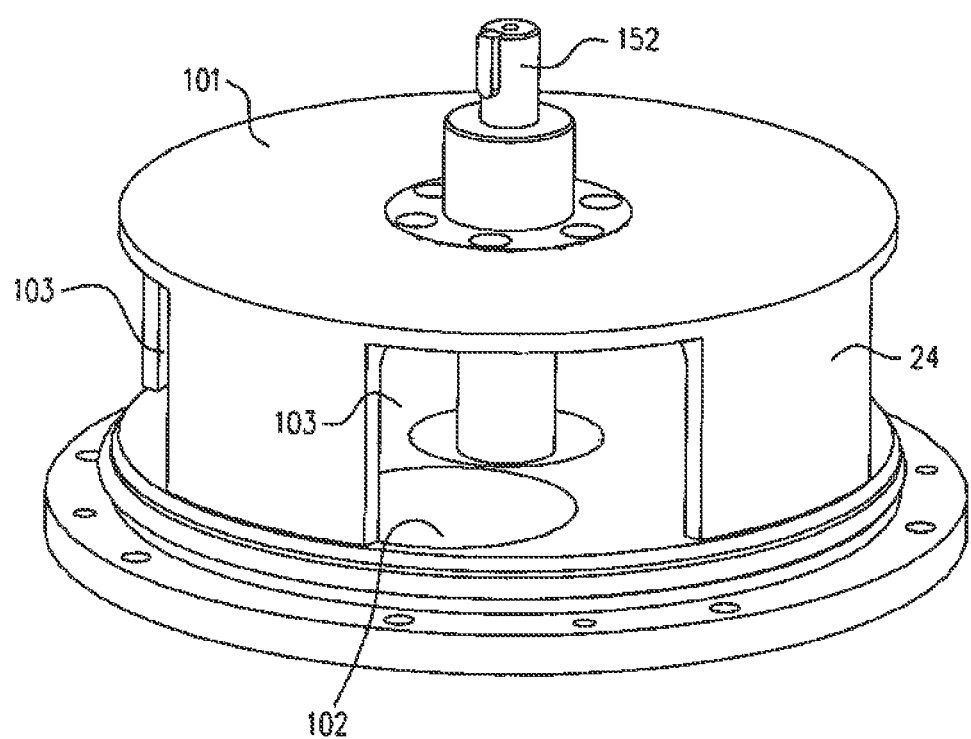
FIG. 4 is a schematic illustration of a fluid-control container of the fluid control assembly of FIG. 3, in accordance with an application of the present invention.

FIG. 4 is a schematic illustration of fluid-control container 101, in accordance with an application of the present invention. Fluid-control container 101 is shaped so as to define a fluid-control container port 102 and a first interface surface 24. First interface surface 24 is shaped so as to define one or more fluid-control container apertures 103. For some applications, such as shown in FIGS. 1-4, first interface surface 24 is cylindrical.

Reference is again made to FIG. 3. Fluid controller 22 is shaped so as to define a second interface surface 26, which is shaped so as to define one or more controller ports 28. Fluid-control container 101, fluid controller 22, and motor 151 are arranged to effect relative translation between first and second interface surfaces 24 and 26, thereby effecting a time-varying overlap between at least a subgroup of fluid-control container apertures 103 and at least a subgroup of controller ports 28. Whenever one of the apertures overlaps a given port, fluid flows through the aperture into the port, causing a relative increase in fluid pressure within the fixture connected to the port. Whenever none of the apertures overlaps a given port, first interface surface 24 blocks fluid flow into the port, causing a relative decrease in fluid pressure within the fixture connected to the port. For some applications, such as shown in FIGS. 1-4, second interface surface 26 is cylindrical. A portion of first surface 24 in a vicinity of apertures 103 and a portion of second surface 26 in a vicinity of ports 28 are disposed facing each other, typically separated by a distance of at least no more than 2 mm (e.g., touching), and/or at least 0.5 mm, and/or between 0.5 mm and 2 mm.

For some applications, at least one (e.g., all) of apertures 103 is shaped so as to define a rectangle, such as shown in FIGS. 3 and 4, and FIGS. 5A-B, described hereinbelow. Alternatively or additionally, for some applications, at least one (e.g., all) of apertures 103 is shaped so as to define an ellipse, e.g., a circle (configuration not shown). Rectangular apertures, which abruptly widen, provide a more abrupt fluid pulse than do elliptical apertures, which gradually widen. Rectangular apertures thus enable higher frequency testing, because they minimize the rise- and fall-time of the fluid pulses. More generally, for some applications, at least one (e.g., all) of apertures is shaped so as to define: (a) a straight leading edge, oriented at an angle of at least 45 degrees, typically at least 80 degrees (e.g., 90 degrees), with a direction of motion of first and second interface surfaces 24 and 26 with respect to each other; and/or (b) a straight trailing edge, oriented at an angle of at least 45 degrees, typically at least 80 degrees (e.g., 90 degrees), with a direction of motion of first and second interface surfaces 24 and 26 with respect to each other. For example, for applications in which at least one of the interface surfaces rotates around a central axis, and the above-mentioned angle is 90 degrees, the leading and/or trailing edges are parallel to the central axis.

For some applications, at least one (e.g., all) of controller ports 28 is shaped so as to define an ellipse, e.g., a circle, such as shown in FIGS. 1-3, and FIGS. 5A-B, described hereinbelow. Alternatively or additionally, for some applications, at least one (e.g., all) of controller ports 28 is shaped so as to define a rectangle (configuration not shown).

(It is to be understood that the shapes mentioned in the previous two paragraphs are not planar for applications in which the first and second surfaces are curved (e.g., cylindrical). For such applications, the shapes are superimposed on these curved surfaces. As used herein, including in the claims, the terms "rectangular," "elliptical," and "circular" include within their respective scopes such curved, non-planar shapes.)

For some applications, apertures 103 and controller ports 28 are shaped such that, as one of the apertures transitions from non-overlapping to overlapping one of the controller ports, the pressure in the fixture connected to the port changes at a rate with respect to time (dp/dt) of at least 100 mmHg/second, such as at least 2,000 mmHg/second, no more than 8,000 mmHg/second, and/or between 100 and 8,000 mmHg/second.

For some applications, fluid-control container 101, fluid controller 22, and motor 151 are arranged such that the motor effects rotation of the fluid-control container with respect to the fluid controller (either by rotating the fluid-control container, the fluid controller, or both the fluid-control container and the fluid controller). Such rotation effects the time-varying overlap between apertures 103 and controller ports 28 described above. Typically, the fluid-control container and the fluid controller are disposed around a common axis. For some, applications, a rotation counter is provided, either as a component of tester 10 or of a controller 200 coupled to tester 10. The rotation counter is configured to count a number of relative rotations of fluid-control container 101 with respect to fluid controller 22 (such as a number of full relative rotations). For some applications, the base (bottom) of fluid-control container 101 rotate as the apertures rotate. For other applications, the base of the fluid-control container does not rotate as the apertures rotate. For these other applications, the base may be coupled to, or an element of, fluid controller 22.

For some applications in which such rotation is implemented, both first and second interface surfaces 24 and 26 are cylindrical, such as shown in FIGS. 1-4. For other applications in which such rotation is implemented, the surfaces are not cylindrical. For example, for these other applications, the surfaces may be planar or curved, e.g., arranged such that one of the surfaces is above the other of the surfaces, assuming the orientation of tester 10 shown in FIGS. 1-4. For applications in which the surfaces are planar, they may define respective planes that, are perpendicular to an axis of fluid control assembly 20 around which the motor effects the rotation of the fluid-control container and/or the fluid controller. For example, the tester may have the configuration described hereinbelow with reference to FIGS. 10A-B.

Reference is made to FIGS. 5A and 5B, which are schematic cross-sectional views of fluid control assembly 20 and fixtures 112 taken along lines VA-VA and VB-VB of FIG. 4, respectively, in accordance with an application of the present invention. Each of fixtures 112 comprises one or more fixture first ports 116 and one or more fixture second ports 117. Fixture first ports 116 are mounted in fluid communication with respective ones of controller ports 28.

Reference is again made to FIGS. 1 and 2. Tester 10 further comprises a fluid pump 121, which comprises first and second pump ports 122 and 123. First pump port 122 is in fluid communication with fixture second ports 117. (Unless otherwise specified, the term "fluid communication," as used in the present application, including the claims, includes both direct and indirect fluid communication.) Second pump port 123 is in fluid communication with fluid-control container port 102, such as via a first fluid guide 131. Optionally, an O-ring is disposed between first fluid guide 131 and fluid-control container port 102.

For some applications, tester 10 further comprises a fixture container 111, which may serve as a fluid reservoir. Fixture container 111 comprises a fixture container port 114, which is in fluid communication with first pump port 122, such as via a second fluid guide 141.

Fixtures 112 are disposed within fixture container 111, such that fixture second ports 117 are in fluid communication (a) with an interior of the fixture container, and (b) with first pump port 122 via the interior of the fixture container and fixture container port 114. For some applications, such as shown in FIGS. 1 and 2, second surface 26 of fluid controller 22 additionally serves as at least one wall of fixture container 111. In the particular configuration shown in FIGS. 1 and 2, second surface 26 serves as an inner cylindrical wall of the fixture container 111 that surrounds fluid-control container 101, and fixture container 111 is generally cylindrical. Other configurations will be evident to those skilled in the art who have read the present application, and are within the scope of the present invention. Fixture container 111 optionally comprises a transparent material, such as glass or plastic.

Typically, for applications in which tester 10 comprises fixture container 111, tester 10 comprises a fluid having a sufficient volume such that a level of the fluid within fixture container 111 is higher than fixture second ports 117. Typically, tester 10 is configured such that fixture container 111 remains stationary during operation of the tester.

For some applications, tester 10 further comprises a pressure relief valve, which is in fluid communication with fluid-control container 101 and/or fixture container 111 (if provided). For some applications, the pressure relief valve is disposed at any location between the second pump port 123 and fluid-control container port 102.

For some applications, e.g., for applications in which fixture container 111 is not provided, fixture second ports 117 are in fluid communication with first pump port 122 via a plurality of tubes (configuration not shown), and, optionally, also via second fluid guide 141. The tubes are coupled to respective ones of the fixture second ports 117.

Tester 10 is typically arranged to define the following continuous loop fluid flow path:
  pump 121,
  second pump port 123,
  fluid-control container port 102,
  fluid-control container 101,
  fluid-control container apertures 103,
  controller ports 28,
  fixture first ports 116,
  fixtures 112,
  fixture second ports 117,
  optionally, fixture contain 111 and fixture container port 114,
  first pump port 122, and
  pump 121.
Additional fluid-conveying elements (e.g., tubes, pipes, hoses, valves, and/or seals) may optionally be provided between the above-listed elements of the fluid flow path.

The direction of the fluid flow path is determined at least in part by the configuration of pump 121. For some applications, pump 121 is configured to pump fluid out of second pump port 123, such that the fluid flows through the above-listed elements in the order in which they are listed above. For other applications, pump 121 is configured to pump fluid out of first pump port 122, such that the fluid flows in a direction opposite the order listed above. For some applications, tester 10 is configured to allow the operator to select the direction of flow, such as manually; typically, any given test of a set of medical devices is performed using a pre-selected directionality. Alternatively, the tester may be programmable to periodically change the direction during a given test, e.g., once every hour, day, or week. For example, a 300-million cycle test at 80 Hz may be complete in approximately 1.5 months.

When pump 121 is configured to pump fluid out of second pump port 123, the second pump port serves as an outlet from the pump. Fluid thus flows through tester 10 along the following flow path:
  out of the outlet (second pump port 123),
  into fluid-control container port 102, which thus serves as a container input port,
  into fluid-control container 101,
  through fluid-control container apertures 103, such that fluid-control container 101 serves as a fluid-distribution container,
  through controller ports 28, such that fluid controller 22 serves as a fluid distributor,
  into fixture first ports 116, which thus serve as fixture input ports,
  into fixtures 112,
  out of fixture second ports 117, which thus serve as fixture output ports,
  optionally, into fixture container 111 (which thus serves as a fluid return container) and out of fixture container port 114, and
  into first pump port 122, which thus serves as an inlet of the fluid pump.
As mentioned above, additional fluid-conveying elements (e.g., tubes, pipes, hoses, valves, and/or seals) may optionally be provided between the above-listed elements of the fluid flow path.

When pump 121 is configured to pump fluid out of first pump port 122, the first pump port serves as an outlet from the pump. Fluid thus flows through tester 10 along the following flow path:
  out of the outlet (first pump port 122),
  optionally, into fixture container port 114 and fixture container 111,
  into fixture second ports 117, which thus serve as fixture input ports,
  into fixtures 112,
  out of fixture first ports 116, which thus serve as fixture output ports,
  through controller ports 28,
  through fluid-control container apertures 103,
  into fluid-control container 101,
  out of fluid-control container port 102, which thus serves as a container output port, and
  into second pump port 123, which thus serves as an inlet of the fluid pump.
As mentioned above, additional fluid-conveying elements (e.g., tubes, pipes, hoses, valves, and/or seals) may optionally be provided between the above-listed elements of the fluid flow path.

Typically, during steady-state operation of the tester, fluid pump 121 is configured to exclusively pump fluid out of exactly one of the first and second pump ports throughout at least one period having a duration of at least one second, such as at least one minute, one hour, or one week. As a result, throughout steady-state operation, fluid flows through each of fixtures 112 in a single direction. In contrast, in some commercially-available testers (such as those that use transducers for fluid pulsation), the direction of fluid flow through test fixtures alternates at high frequency, such as at least several times per second, e.g., at 10-20 Hz. Such high-frequency reversal of fluid-flow direction may cause noise and heat, and may limit the maximum frequency at which these commercially-available testers can operate.

For some applications, such as in order to provide substantial back-flow, at least one of fixtures 112 is coupled in fluid communication with fluid-control container 101 at both ends of the fixture (i.e., both fixture first port 116 and fixture second port 117), at different respective rotational positions around the fluid-control container. As a result, at a first rotational orientation of the fluid-control container, a fluid pulse is pushed through a first end of the fixture (toward the fixture's second end), and at a second rotational orientation of the fluid-control container, a fluid pulse is pushed through the second end of the fixture (toward the fixture's first end).

For some applications, motor 151 is in mechanical communication with fluid-control container 101, such as shown in FIGS. 1-4. For some applications, fluid-control container 101 and motor 151 are arranged such that the motor effects rotation of the fluid-control container, such as described hereinabove. For some applications, fluid control assembly 20 further comprises a motor shaft 152 (labeled in FIG. 4), a first end of which is coupled to the motor, and a second end of which is coupled to the fluid-control container.

For other applications, motor 151 is in mechanical communication with fluid controller 22 (configuration not shown). For some applications, fluid controller 22 and motor 151 are arranged such that the motor effects rotation of the fluid controller. For some applications, fluid control assembly 20 further comprises a motor shaft, a first end of which is coupled to the motor, and a second end of which is coupled to the fluid controller.

For some applications, tester 10 further comprises a heating element, which is in fluid communication with fixture container 111 and/or fluid-control container 101. For some applications, the heating element may be disposed near the bottom of fixture container 111. For some applications, a user interface of controller 200 is configured to enable setting of operational parameters of the heating element so as to maintain a temperature of fluid within the tester, typically within a user-defined range. For example, the user-defined range may have a lower limit of between 35 and 37 degrees centigrade (e.g., 36 degrees) and a higher limit of between 37 and 39 degrees centigrade (e.g., 38 degrees). (In general, controller 200 comprises one or more processors and memory, and may, for example, comprise a standard PC or workstation with appropriate software for carrying out the functions described herein.)

For some applications, tester 10 further comprises a pressure sensor, which is in fluid communication with fluid-control container 101 and/or fixture container 111 (if provided). For some applications, the pressure sensor is disposed at a location between first pump port 122 and controller ports 28. Typically, the pressure sensor is place equidistant from all of the controller ports and at the same vertical level as the controller ports (so as to measure actual pressure, including gravitational effects on the fluid). For some applications, a signal-conditioning circuit is further provided, either as a component of tester 10 or controller 200. For some applications, the signal-conditioning circuit is configured to convert an output of the pressure sensor for display on a graphical user interface, either of tester 10 or of controller 200. For some applications, a processing unit is provided, which is coupled to the signal-conditioning circuit, and which is configured to control a speed of the motor, and/or an output level of the pump, so as to maintain a value of a fluid pressure within a user-defined range, which value is measured by the pressure sensor. For example, the user-defined range of the fluid pressure may have a lower limit of between 50 and 70 mmHg (e.g., 60 mmHg) and an upper limit of between 160 and 200 mmHg (e.g., 180 mmHg).

Reference is now made to FIGS. 6A-B, which are cross-sectional views of fluid-control container 101 and fluid controller 22 in differing alignments with each other, in accordance with an application of the present invention. In the configuration shown, both first and second interface surfaces 24 and 26 are cylindrical, and fluid-control container 101 and fluid controller 22 are arranged to rotate with respect to each other, as described hereinabove. Such rotation effects the time-varying overlap between apertures 103 and controller ports 28 described hereinabove with reference to FIG. 3. Alternatively, the time-varying overlap is effected without rotation, and/or the first and second surfaces are not cylindrical. For example, the first and second surfaces may both be generally planar and rectangular, and/or may slide linearly with respect to each other. The applications described below may be implemented both for rotating and/or cylindrical configurations, or for other non-rotating and/or non-cylindrical configurations.

For some applications, apertures 103 are generally equally spaced along first interface surface 24, and/or controller ports 28 are generally equally spaced along second interface surface 26. For applications in which both the apertures and the controller ports are generally equally spaced, the time-varying overlap between the apertures and the controller ports repeats at a constant frequency, assuming the motor effects relative translation between the first and second interface surfaces at a constant rate.

For some applications, the overlap periodically varies at a rate of at least 10 Hz, no more than 200 Hz, and/or between 10 to 200 Hz, such as at least 20 Hz, no more than 150 Hz, and/or between 20 and 150 Hz, e.g., at least 40 Hz, no more than 120 Hz, and/or between 40 and 120 Hz, or at least 60 Hz, no more than 100 Hz, and/or between 60 and 100 Hz, e.g., 80 Hz. For some applications, the tester is calibrated using operation at 1 Hz as a benchmark, to verify that a physiologically-reliable pressure waveform is obtained at the tester's actual operating frequency, similar to the waveform obtained at 1 Hz. For some applications, medical devices are tested in vitro for the equivalent of at least 10 years of cardiac cycles (e.g., at least 380 million cycles), such as at a frequency of 80 Hz. Other time periods may of course be used, such as specified by applicable regulatory and/or quality control requirement or standards. For some applications, the tester is activated for at least 30 million cycles.

First interface surface 24 is shaped so as to define a first number of apertures 103, and second interface surface 26 is shaped so as to define a second number of controller ports 28. For some applications, the first number is less than the second number, as shown in FIGS. 6A-B. For example, the first number may be less than 50% of the second number, and/or the ratio of the first number to the second number may be less than 7:8, at least 1:10, and/or between 1:10 and 7:8. For example, the first number may be 4 and the second number may be 6, as shown in FIGS. 6A-B. For some applications, providing fewer apertures than ports enables a single fixture to be coupled to two ports on the same level, such as described hereinbelow with reference to FIG. 11; the ratio of apertures to ports provides an additional parameter for controlling the systole/diastole duty cycle. Alternatively, the first number may be equal to the second number. Further alternatively, the first number may be greater than the second number, such as at least 200% of the second number, and/or the ratio of the first number to the second number may be less than 10:1, at least 8:7, and/or between 8:7 and 10:1.

In general, for applications in which the number of apertures does not equal the number of ports, the pressure increases in different ones of the fixtures at any given point in time. For applications in which there are an equal number of apertures and ports, the pressure increases in all of the fixtures at the same time, assuming that the apertures and ports are similarly spatially distributed on the respective interface surfaces. For some applications, all of the apertures are aligned with the ports at the same time, such that all of the fixtures and medical devices simultaneously experience the same pressure dynamics. For other applications, the apertures and ports are arranged to provide a phase shift between the "systole" of the different fixtures, for example between the fixtures at a first level and the fixtures at a second level, as described hereinbelow with reference to FIGS. 8 and 9A-B. This latter arrangement may be particularly appropriate for applications in which there are a large number of fixtures, and the pump has insufficient power to simultaneously provide increased pressure in all of the fixtures.

Figure 7A:
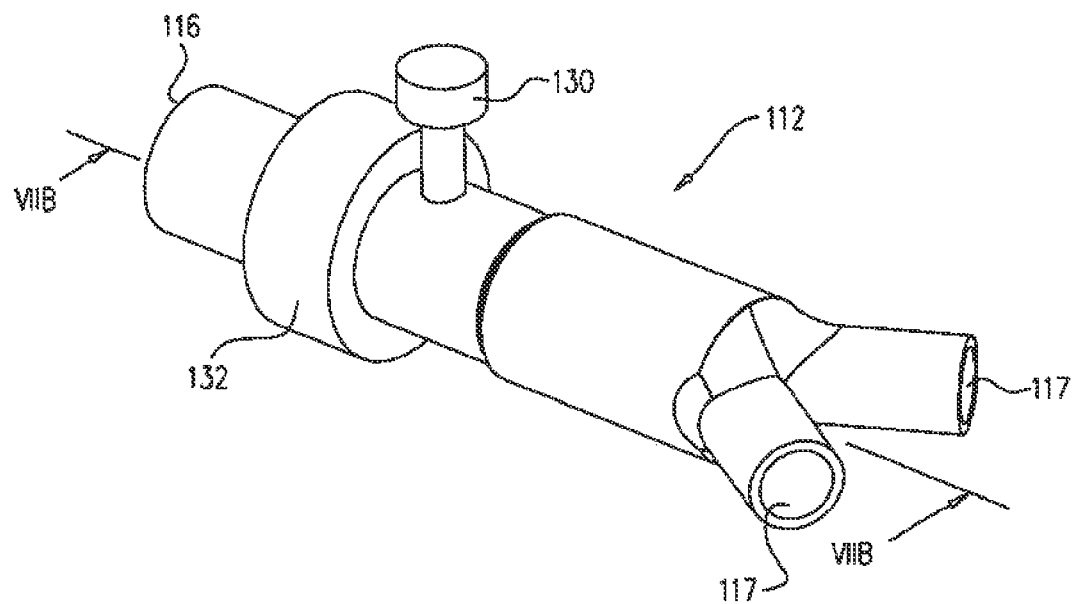
FIGS. 7A-B are schematic illustrations of one of the fixtures of FIGS. 1-2, in accordance with an application of the present invention.
Figure 7B:
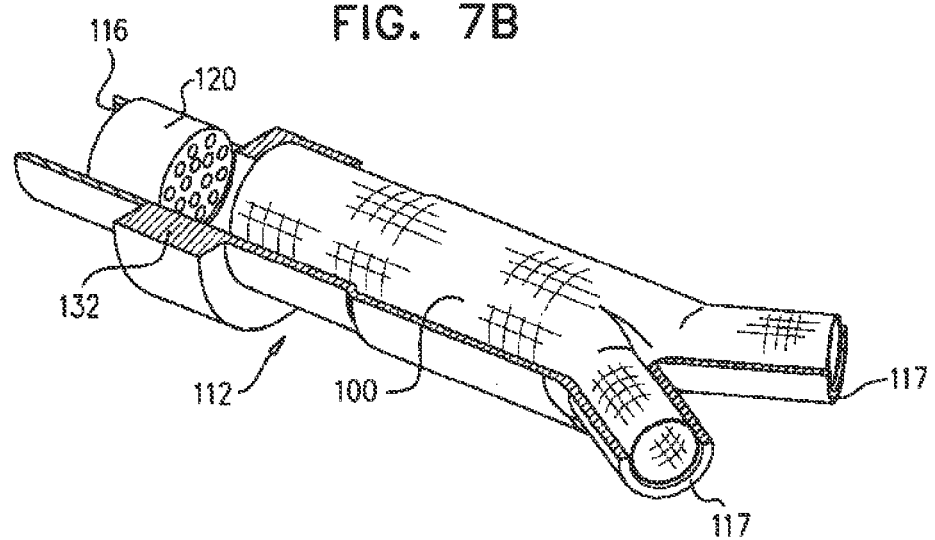

Reference is made to FIGS. 7A-B, which are schematic illustrations of one of fixtures 112, in accordance with an application of the present invention. As mentioned above, fixtures 112 are configured to allow disposition therewithin of medical devices, such as complete medical devices or medical device components. For example, an exemplary medical device 100 comprising a bifurcated stent is shown disposed within the fixture shown in cross-section in FIG. 7B. For some applications, the fixtures are generally tubular. The fixtures may comprise, for example, glass or metal. Typically, a volume of each of fixtures 112 is at least 30 ml, no more than 400 ml, and/or between 30 and 400 ml, such as at least 40 ml, no more than 200 ml, and/or between 40 and 200 ml, such as at least 50 ml, no more than 150 ml, and/or between 50 and 150 ml, such as 85 ml. For some applications, a port 130 is provided for insertion of a pressure measurement probe. For some applications, an adapter 132 is provided for connecting flow straighteners 120 (described below) with different types of device fixtures. For example, the adapter may be shaped so as to define a cylindrical section with an inner thread.

For some applications, one or more (e.g., all) of fixtures 112 comprise respective flow straighteners 120, which are positioned near fixture first ports 116 (either within the fixtures, or immediately adjacent to the fixtures), such that fluid flows through the straightener before reaching the area of the fixture in which medical device 100 is disposable. Flow straighteners 120 are configured to cause the fluid to flow through the fixtures generally parallel to respective longitudinal axes of the fixtures, by removing a large portion of the vertical and horizontal rotational momentum from the radially-oriented fluid. For some applications, each flow straightener comprises a plurality of parallel tubes. For example, the tubes may have an aspect ratio (i.e., a ratio between length and inner diameter) of at least 10. The flow straighteners may be generally cylindrical.

Figure 9A:
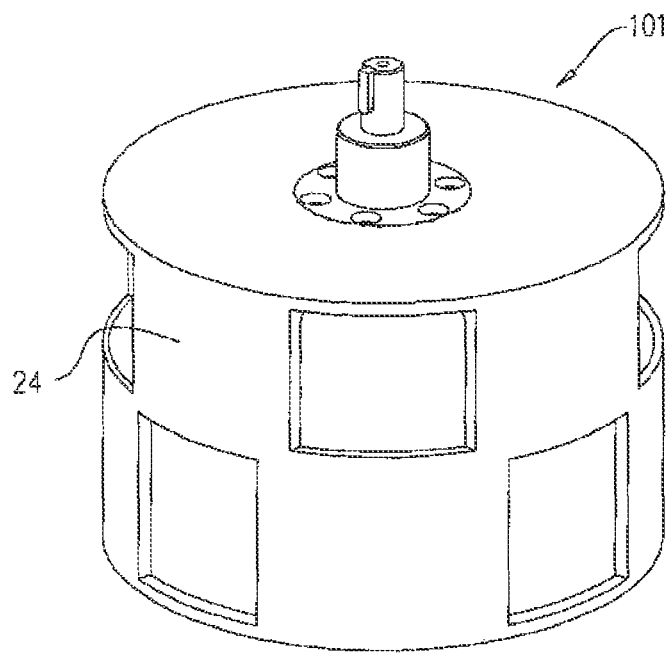
Figure 9B:
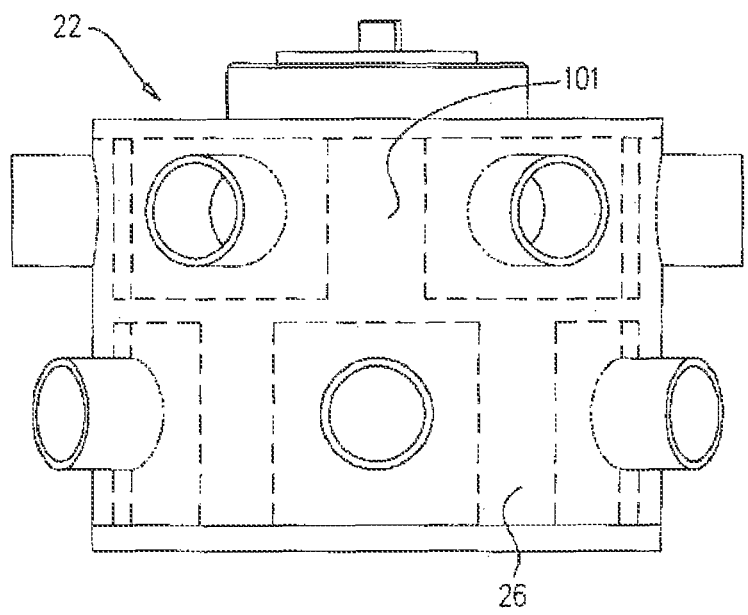

Reference is now made to FIGS. 8 and 9A-B, which are schematic illustrations of an alternative configuration of tester 10, in accordance with an application of the present invention. Except as described below, this configuration is generally similar to the configurations described hereinabove. FIG. 8 shows the assembly of fluid-control container 101, fluid controller 22, and fixtures 112. FIG. 9A shows fluid-control container 101, while FIG. 9B shows fluid controller 22 (with fluid-control container 101 visible therewithin).

In this configuration, first interface surface 24 of fluid-control container 101 is shaped so as to define two rows of apertures 103, and second interface surface 26 of fluid controller 22 is shaped so as to define two circumferential arrays of controller ports 28, at respective, different axial locations (such as upper and lower circumferential arrays, as shown in FIGS. 8 and 9A-B). This configuration allows a greater number of fixtures 112 to be provided, without increasing the diameters of fluid-control container 101 and fluid controller 22. In addition, by providing fewer apertures than ports, this configuration may enable testing at respective, different frequencies in the circumferential arrays. More than two circumferential arrays of apertures and controller ports may also be provided (configuration not shown).

Figure 10A:
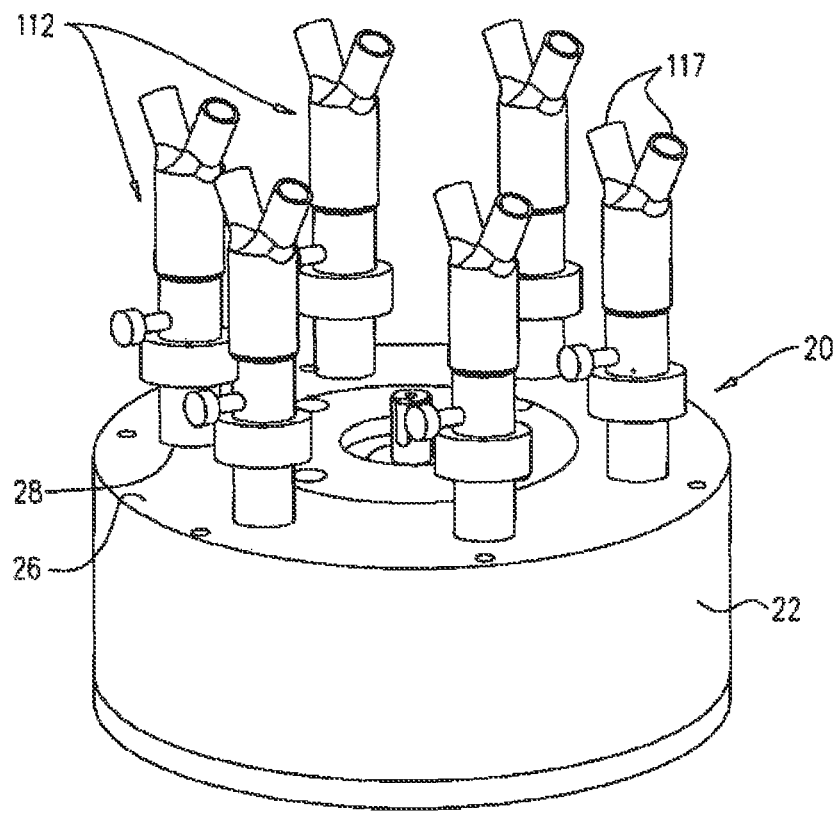
FIGS. 10A-B are schematic illustrations of a portion of a fluid control assembly and fixtures of the tester of FIG. 1-2, and of a fluid-control container of the tester, respectively, in accordance with an application of the present invention.
Figure 10B:
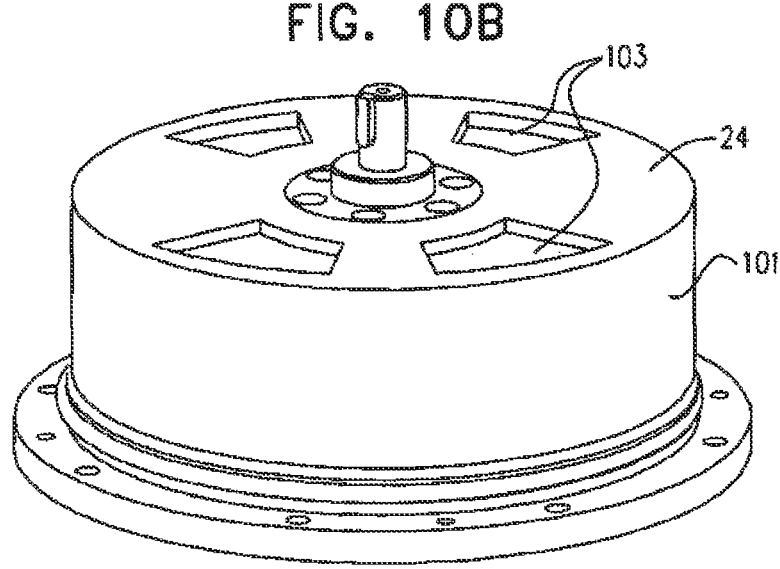

Reference is now made to FIGS. 10A-B, which are schematic illustrations of a portion of fluid control assembly 20 and fixtures 112, and of fluid-control container 101, respectively, in accordance with an application of the present invention. This configuration may be used for applications in which fluid-control container 101, fluid controller 22, and motor 151 are arranged such that the motor effects rotation of the fluid-control container with respect to the fluid controller, as described hereinabove with reference to FIGS. 1-4. In this configuration, interface surfaces 24 and 26 are typically planar, and define respective planes that are perpendicular to an axis of fluid control assembly 20 around which motor 151 effects the rotation of the fluid-control container and/or the fluid controller.

For some applications, as shown in FIG. 10A, interface surfaces 24 and 26 are arranged such that second interface surface 26 is positioned above and parallel to first interface surface 24. Fluid-control container 101 is thus shaped so as to define first interface surface 24 (and apertures 103) on a top surface of container 101, e.g., generally parallel with a surface on which tester 10 is placed, and fluid controller 22 is shaped so as to define second interface surface 26 (and controller ports 28) on a top surface of controller 22, e.g., also generally parallel with the surface on which tester 10 is placed. Because fixture first ports 116 of fixtures 112 are mounted in fluid communication with respective ones of controller ports 28, the fixtures extend from the top surface of the fluid controller, such as generally vertically (as shown), or generally upward at an angle (configuration not shown). Alternatively, the fluid flow paths from ports 28 to fixtures 112 are curved, such that the fixtures extend outward horizontally, such as shown in FIGS. 1-4.

Alternatively, fluid control assembly 20 is oriented in a different direction from that shown in FIGS. 10A-B. For example, the assembly may be inverted 180 degrees (upside-down), or between 0 and 180 degrees (to the side). Further alternatively or additionally, the first and second surfaces may not be planar, but may be instead curved.

Reference is now made to FIG. 11, which is a schematic illustration of an alternative configuration of fixture 112, in accordance with an application of the present invention. This configuration may be used with any of the configurations of tester 10 described herein. In this configuration, at least one of fixtures 112 is shaped so as to define at least two (e.g., exactly two) fixture first ports 116, and, typically, at least two (e.g., exactly two) fixture second ports 117. Typically, the two fixture first ports 116 are positioned near (e.g., within a distance equal to 5 times a square root of an average cross-sectional area of the fixture, and/or within 10 mm of the ends) opposite ends of the fixture from each other (typically, such that the two fixture first ports are in direct fluid communication with the respective ends of the fixture), and the two fixture second ports 117 are positioned near (e.g., within a distance equal to 10 times a square root of an average cross-sectional area of the fixture, and/or within 20 mm of the ends) opposite ends of the fixture from each other (typically, such that the two fixture second ports are in direct fluid communication with the respective ends of the fixture). The fixture first ports 116 are typically mounted in fluid communication with respective ones of controller ports 28. For example, fixture first ports 116 may be mounted in fluid communication with adjacent ones of the controller ports, as shown in FIG. 11.

Alternatively, first and second ones of fixture first ports 116 may be mounted in fluid communication with controller ports of first and second circumferential arrays, respectively, as described hereinabove with reference to FIGS. 8 and 9A-B.

Typically, fluid control assembly 20 is configured, to allow fluid flow to fixture first ports 116 with a timing offset. Alternatively, the fluid control assembly is configured to allow fluid flow to both fixture first ports simultaneously.

Figure 12:
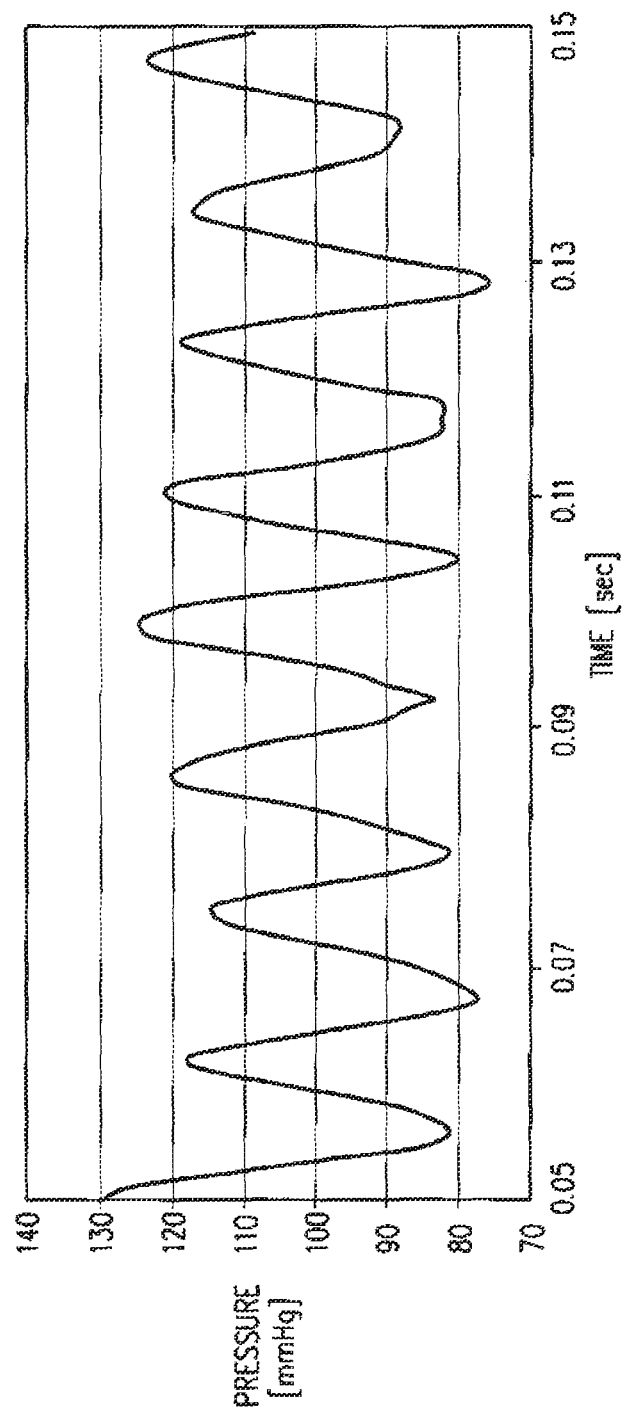
FIG. 12 is a graph showing a pressure wave, measured in accordance with an application of the present invention.

Reference is made to FIG. 12, which is a graph showing a pressure wave, measured in accordance with an application of the present invention. The pressure wave was measured during operation of a prototype implementation of tester 10, using an integrated PC-based data acquisition system. The tester had a capacity of approximately 100 liters, and was filled with approximately 50 liters of fluid during measurement of the pressure wave. The tester comprised six fixtures 112, each of which had a volume of 85 cc, for a total volume of 510 cc (about 0.5 liters). Medical devices 100 were not placed in the fixtures during measurement.

It can be seen that the pressure peaks and troughs have physiological values (generally fluctuating between about 80 mmHg and 130 mmHg), except that their rate is about two orders of magnitude greater than a typical physiological blood pressure cycle rate (8 cycles in a 0.1 second-period, i.e., 80 Hz, compared to a 1 Hz typical heart rate). This high rate was achieved in a large tester, as described above.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for fatigue testing one or more medical devices, the apparatus comprising:
   a fluid control assembly, which comprises:
      a fluid-control container, which is shaped so as to define a fluid-control container port and a first interface surface that is shaped so as to define one or more fluid-control container apertures;
      a fluid controller, which is shaped so as to define a second interface surface that is shaped so as to define one or more controller ports; and
      a motor,
      wherein the fluid-control container, the fluid controller, and the motor are arranged to effect relative translation between the first and second interface surfaces, thereby effecting a time-varying overlap between at least a subgroup of the fluid-control container apertures and at least a subgroup of the controller ports;
   one or more fixtures, configured to allow disposition therewithin of respective ones of the medical devices, each of which fixtures comprises one or more fixture first ports and one or more fixture second ports, which fixture first ports are mounted in fluid communication with respective ones of the controller ports; and
   a fluid pump, which comprises first and second pump ports, which are in fluid communication with the fixture second ports and the fluid-control container port, respectively.

2. The apparatus according to claim 1, wherein, throughout steady-state operation of the apparatus, the fluid pump is configured to exclusively pump fluid out of exactly one of the first and second pump ports throughout at least one period having a duration of at least one second.

3. The apparatus according to claim 1, wherein, throughout steady-state operation of the apparatus, the fluid pump is configured to exclusively pump fluid out of exactly one of the first and second pump ports throughout a test of the medical devices.

4. The apparatus according to claim 1, wherein the apparatus is configured to cyclically increase and decrease a pressure of a fluid within the fixtures during a plurality of cycles.

5. The apparatus according to claim 4, wherein, throughout steady-state operation of the apparatus, the fluid pump is configured to exclusively pump fluid out of exactly one of the first and second pump ports throughout at least one of the cycles.

6. The apparatus according to claim 1, wherein the fluid pump is configured to receive fluid via the first pump port, which thus serves as an inlet, and to pump the fluid out of the second pump port, which thus serves as an outlet, such that the fluid flows through the apparatus along a flow path:
   out of the outlet,
   into the fluid-control container port, which thus serves as a container input port,
   through the fluid-control container apertures, such that the fluid-control container serves as a fluid-distribution container,
   through the controller ports, such that the fluid controller serves as a fluid distributor, into the fixture first ports, which thus serve as fixture input ports, out of the fixture second ports, which thus serve as fixture output ports, and into the inlet of the fluid pump.

7. The apparatus according to claim 1, wherein the overlap periodically varies at a rate of 10 to 150 Hz.

8. The apparatus according to claim 1, wherein the first and second interface surfaces are cylindrical.

9. The apparatus according to claim 1, wherein the first and second interface surfaces are planar.

10. The apparatus according to claim 9, wherein the fluid-control container, the fluid controller, and the motor are arranged such that the motor effects rotation of the fluid-control container with respect to the fluid controller, and wherein the first and second interface surfaces define respective planes that are perpendicular to an axis of the fluid control assembly around which the motor effects the rotation.

11. The apparatus according to claim 1, wherein the apparatus further comprises a fixture container, which is shaped so as to define a fixture container port that is in fluid communication with the first pump port, wherein the fixtures are disposed within the fixture container, such that the fixture second ports are in fluid communication with an interior of the fixture container, and with the first pump port via the interior of the fixture container and the fixture container port.

12. The apparatus according to claim 11, wherein the apparatus further comprises a fluid having a sufficient volume such that a level of the fluid within the fixture container is above a level of the fixture second ports.

13. The apparatus according to claim 11, wherein the fixture container is shaped so as to define a plurality of walls, and wherein the apparatus is configured such that the second surface serves as at least one of the walls of the fixture container.

14. The apparatus according to claim 1, wherein the fluid-control container, the fluid controller, and the motor are arranged such that the motor effects rotation of the fluid-control container with respect to the fluid controller.

15. The apparatus according to claim 14, wherein the fluid-control container, the fluid controller, and the motor are arranged such that the motor effects the rotation of the fluid-control container.

16. The apparatus according to claim 14, wherein the fluid-control container, the fluid controller, and the motor are arranged such that the motor effects the rotation of the fluid controller.

17. The apparatus according to claim 14, wherein the fluid-control container and the fluid controller are disposed around a common axis.

18. The apparatus according to claim 1, wherein the motor is in mechanical communication with the fluid-control container.

19. The apparatus according to claim 18, wherein the fluid-control container and the motor are arranged such that the motor effects rotation of the fluid-control container.

20. The apparatus according to claim 1, wherein the motor is in mechanical communication with the fluid controller.

21. The apparatus according to claim 20, wherein the fluid controller and the motor are arranged such that the motor effects rotation of the fluid controller.

22. The apparatus according to claim 1, wherein the fluid-control container apertures are generally equally spaced along the first interface surface.

23. The apparatus according to claim 1, wherein the distributor ports are generally equally spaced along the second interface surface.

24. The apparatus according to claim 1, wherein at least one of the fluid-control container apertures is shaped so as to define a rectangle.

25. A method comprising:
provinding a biomedical tester, which includes (a) a fluid control assembly, which includes (i) a fluid-control container, which is shaped so as to define a fluid-control container port and a first interface surface that is shaped so as to define one or more fluid-control container apertures, (ii) a fluid controller, which is shaped so as to define a second interface surface that is shaped so as to define one or more controller ports, and (iii) a motor, wherein the fluid-control container, the fluid controller, and the motor are arranged to effect relative translation between the first and second interface surfaces, thereby effecting a time-varying overlap between at least a subgroup of the fluid-control container apertures and at least a subgroup of the controller ports; (b) one or more fixtures, configured to allow disposition therewithin of respective ones of the medical devices, each of which fixtures comprises one or more fixture first ports and one or more fixture second ports, which fixture first ports are mounted in fluid communication with respective ones of the controller ports; and (c) a fluid pump, which comprises first and second pump ports, which are in fluid communication with the fixture second ports and the fluid-control container port, respectively;
disposing one or more medical devices in respective ones of the fixtures of the biomedical tester; and
activating the biomedical tester to test the one or more medical devices.

26. The method according to claim 25, wherein the biomedical tester is configured to cyclically increase and decrease a pressure of a fluid within the fixtures during a plurality of cycles, and wherein activating comprises activating the biomedical tester for at least 30 million of the cycles.

27. The method according to claim 25, wherein activating the biomedical tester comprises activating the biomedical tester such that, throughout steady-state operation of the biomedical tester, the fluid pump exclusively pumps fluid out of exactly one of the first and second pump ports throughout at least one period having a duration of at least one second.

28. The method according to claim 25, wherein activating the biomedical tester comprises activating the biomedical tester such that, throughout steady-state operation of the biomedical tester, the fluid pump exclusively pumps fluid out of exactly one of the first and second pump ports throughout a test of the medical devices.

29. The method according to claim 25, wherein activating the biomedical tester comprises activating the biomedical tester to cyclically increase and decrease a pressure of a fluid within the fixtures during a plurality of cycles.

30. The method according to claim 25, wherein activating the biomedical tester comprises activating the biomedical tester such that the overlap periodically varies at a rate of 10 to 150 Hz.

31. The method according to claim 25, wherein providing the biomedical tester comprises:
providing the biomedical tester further including a fixture container, which is shaped so as to define a fixture container port that is in fluid communication with the first pump port, wherein the fixtures are disposed within the fixture container, such that the fixture second ports are in fluid communication with an interior of the fixture container, and with the first pump port via the interior of the fixture container and the fixture container port; and
placing a fluid in the fixture container that has a sufficient volume such that a level of the fluid within the fixture container is above a level of the fixture second ports.

* * * * *